(12) United States Patent
Procop et al.

(10) Patent No.: US 8,101,353 B2
(45) Date of Patent: Jan. 24, 2012

(54) SYSTEM AND METHOD FOR NUCLEOTIDE SEQUENCE PROFILING FOR SAMPLE IDENTIFICATION

(75) Inventors: Gary W. Procop, Twinsburg, OH (US); Wei Wei, Ames, IA (US); Ho-ming Pang, Ames, IA (US)

(73) Assignee: Advanced Analytical Technologies, Inc., Ames, IA (US)

( * ) Notice: Subject to any disclaimer, the term of this patent is extended or adjusted under 35 U.S.C. 154(b) by 0 days.

(21) Appl. No.: 12/338,373

(22) Filed: Dec. 18, 2008

(65) Prior Publication Data

US 2010/0209908 A1    Aug. 19, 2010

Related U.S. Application Data

(60) Provisional application No. 61/014,609, filed on Dec. 18, 2007.

(51) Int. Cl.
    *C12Q 1/68*    (2006.01)
(52) U.S. Cl. ...................................................... 435/6.1
(58) Field of Classification Search .................. None
    See application file for complete search history.

(56) References Cited

U.S. PATENT DOCUMENTS

| | | | |
|---|---|---|---|
| 4,865,968 A | 9/1989 | Orgel et al. | |
| 5,064,754 A | 11/1991 | Mills | |
| 5,308,751 A | 5/1994 | Ohkawa et al. | |
| 5,503,980 A | 4/1996 | Cantor | |
| 5,512,458 A | 4/1996 | Leonard | |
| 5,545,302 A | 8/1996 | Zhu et al. | |
| 5,599,675 A | 2/1997 | Brenner | |
| 5,683,874 A | 11/1997 | Kool | |
| 5,714,318 A | 2/1998 | Sagner et al. | |
| 5,888,780 A | 3/1999 | Dahlberg et al. | |
| 5,952,176 A * | 9/1999 | McCarthy et al. | 435/6 |
| 5,985,556 A | 11/1999 | Kambara et al. | |
| 6,190,868 B1 * | 2/2001 | Rothberg et al. | 435/6 |
| 6,258,544 B1 | 7/2001 | Gupte et al. | |
| 6,294,337 B1 | 9/2001 | Hayashizaki | |
| 6,440,705 B1 * | 8/2002 | Stanton et al. | 435/91.2 |
| 6,537,757 B1 | 3/2003 | Langmore et al. | |
| 6,599,703 B2 | 7/2003 | Jones | |
| 6,833,246 B2 | 12/2004 | Balasubramanian | |
| 7,270,958 B2 | 9/2007 | Makarov et al. | |
| 7,329,492 B2 | 2/2008 | Hardin et al. | |
| 2003/0180769 A1 | 9/2003 | Metzker | |
| 2004/0023279 A1 | 2/2004 | Piepenbrock et al. | |
| 2005/0115837 A1 | 6/2005 | Burgi et al. | |
| 2005/0176007 A1 | 8/2005 | De Leeuw et al. | |
| 2006/0052279 A1 | 3/2006 | Zhu et al. | |

FOREIGN PATENT DOCUMENTS

WO    8605817 A1    10/1986

OTHER PUBLICATIONS

DNA Molecules as Standard Reference Materials I: Development of DNA Identification Sequences and Human Mitochondrial DNA Reference Sequences, vol. 102, No. 1, Jan.-Feb. 1997, Journal of Research of the National Institute of Standards and Technology, p. 53-62.
International Search Report and Written Opinion for International Application No. PCT/US08/87434, dated Sep. 15, 2009, 7 pages.
Rodolfo Negri et. al. "A Single-Reaction Method for DNA Sequence Determination" Analytical Biochemistry vol. 197, pp. 389-395.
Sergio Ferraboli et. al. "One-Lane Chemical Sequencing of 3'-Fluorescent-Labeled DNA" Analytical Biochemistry, vol. 214, pp. 566-570.

* cited by examiner

*Primary Examiner* — Christopher M. Babic

(57) ABSTRACT

The invention includes a method of sample profiling for identification. The method includes the steps of performing less than four nucleotide-specific chemical cleavage reactions to obtain nucleotide sequence fragments, performing size separation on the fragments, detecting the fragments' separation, generating a profile based on the detection, and comparing the profile to a data base to identify the sample.

15 Claims, 9 Drawing Sheets

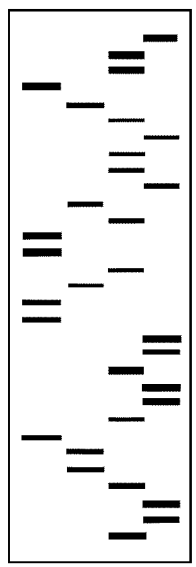
Fig. 1A
*Prior Art*
G A T C
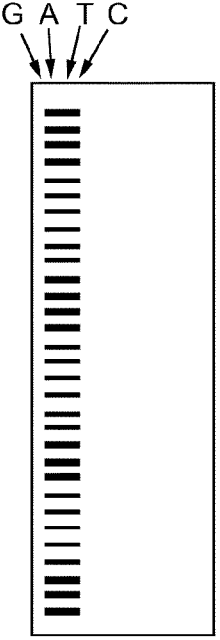
Fig. 1B
*Prior Art*
G A T C
Fig. 2
*Prior Art*
T C A A A T T T T G A G T T G C A T C C C C T G G
   290                         300                       310
(SEQ ID NO. 54)
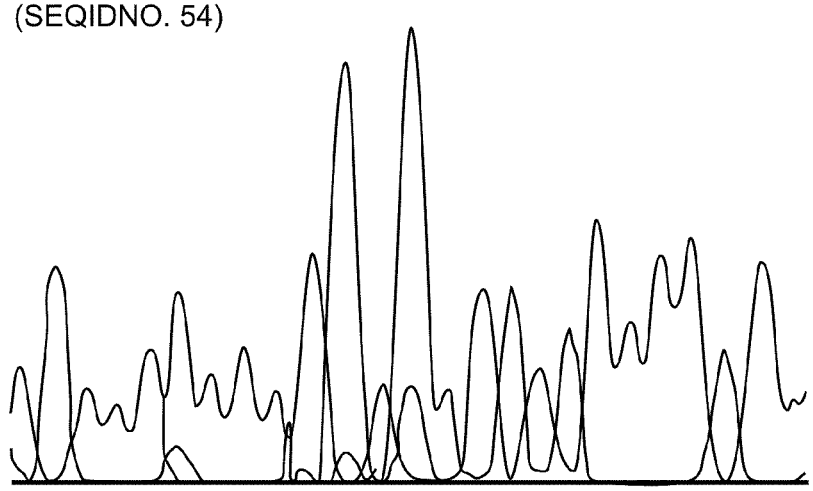

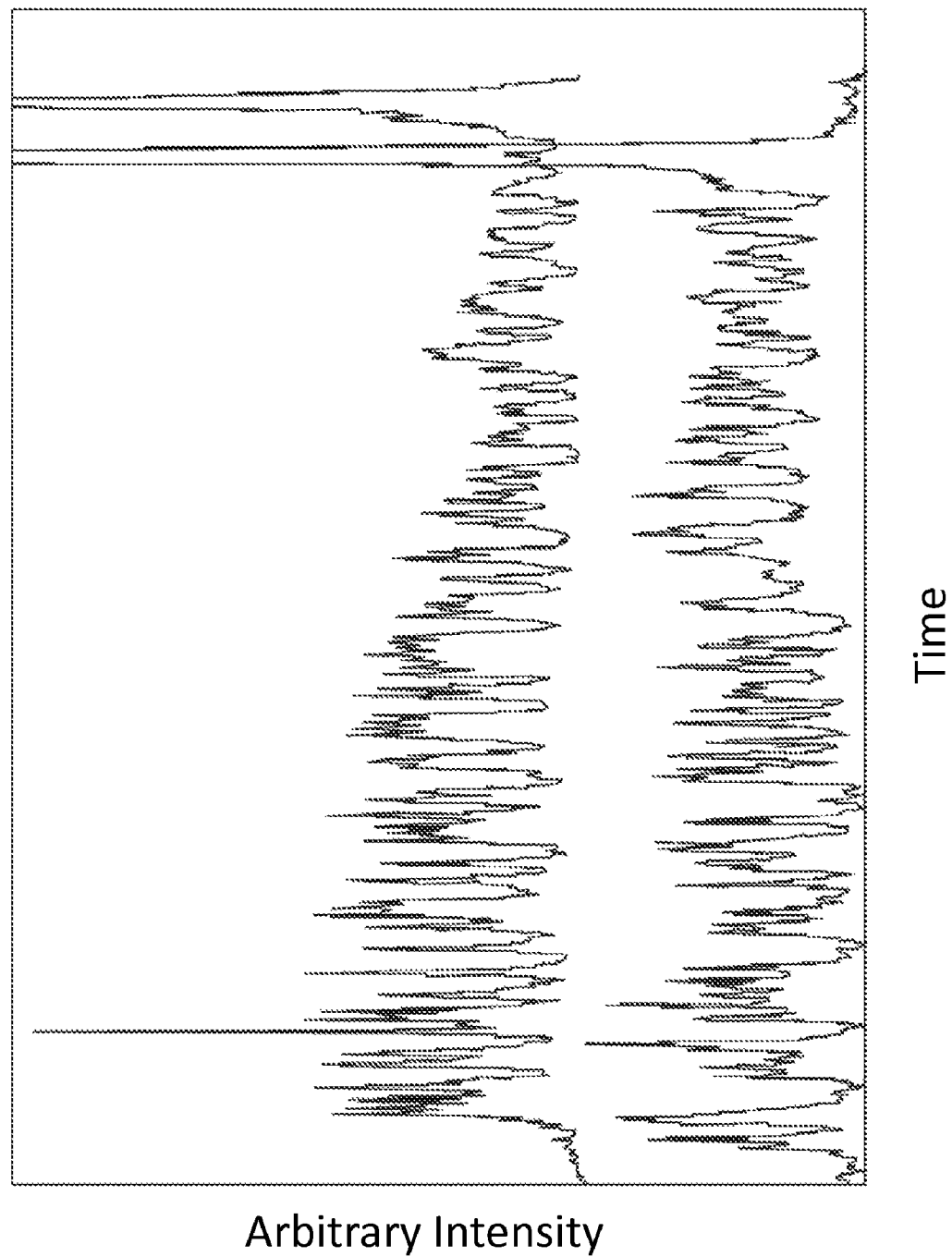

USSYSTEM AND METHOD FOR NUCLEOTIDE
SEQUENCE PROFILING FOR SAMPLE
IDENTIFICATION

RELATED APPLICATIONS

This application claims the benefit of U.S. Provisional Application Ser. No. 61/014,609, titled System and Method for DNA Profiling for Microorganism Identification, filed Dec. 18, 2007, the contents of which are hereby incorporated by reference.

FIELD OF THE INVENTION

The invention relates to the identification of samples by nucleotide sequence profiling.

BACKGROUND OF THE INVENTION

Traditionally biochemical and phenotypic techniques have been used for microorganism identification. The conventional methods for microorganism identification are based on isolation, cultivation, colonial morphology, and subsequent biochemical testing (e.g., oxidase production and glucose fermentation). These methods, although effective, are slow and typically take more than 24 hours to generate enough data to achieve an accurate identification. In addition, they usually are not discriminatory enough to provide sub-species identification. Furthermore, numerous different types of biochemical reactions must be maintained in a quality manner in the laboratory to correctly identify the sundry bacteria that may be encountered in a clinical specimen. Fortunately, these are now commercially-available in a variety of identification kits. Although commercial identification products most often represent a distinct advance over traditional tube testing, they are costly and errors in identification may occur.

Recently, genotypic techniques have emerged as the preferred methods for microorganism identification, because of the high-degree of accuracy provided, when DNA sequencing is used in conjunction with a sufficiently discriminating genetic target. There are inherent advantages of using nucleic acid sequencing information for the identification of microorganisms, and this is considered by many the "gold standard" for taxonomic categorization. In most instances, the microorganism is cultured and the DNA is extracted from the microorganism and submitted for the polymerase chain reaction (PCR). The PCR amplifies a section of genome that is characterized through the traditional DNA sequencing reaction (i.e. Sanger sequencing).

In brief, PCR amplification uses two primers that hybridize to opposite strands of a specific DNA section. The primers are oriented so that the elongation reaction proceeds from 5' to 3' across the region between the two primers. These primers are often designed to hybridize to conserved regions in the bacterial or fungal genome (i.e., they are broad-range primers). In addition, they are designed to flank a region or regions that contain sufficient sequence variation to afford organism characterization. The PCR product is then submitted to the Sanger sequencing reaction (i.e., enzymatic chain elongation/termination through the incorporation of di-deoxyribonucleotide triphosphate [ddNTP] incorporation). In a commonly used method, the products of the Sanger reaction each have one of the four ddNTPs at the terminus of the DNA strand and the four ddNTP molecules are labeled with different fluorophores. The products are then separated by electrophoresis and differentiated with laser-induced fluorescence detection. Another method to label the Sanger reaction products for detection uses a fluorescently-labeled primer. In this case, only one ddNTP is used to terminate the reaction. Four different reactions, each with a different ddNTP, are used to determine the DNA sequence. The reactions products from the four reactions are pooled, then electrophoretic separation and detection is performed.

It is not necessary to perform DNA sequencing for microorganism identification with enzymatic chain elongation reaction. Maxam and Gilbert have developed a sequencing method based on chemical reactions. This reaction procedure determines the nucleotide sequence of a terminally labeled DNA molecule by random breaking at adenine (A), guanine (G), cytosine (C), or thymine (T) positions using specific chemical agents. This method initially modified the DNA with base-specific modification reactions then followed by the removal of the modified base from its sugar and cleaved the DNA strand at that sugar position. For each breakage, two fragments are generated from each strand of DNA. In order to perform a sequencing analysis, only one fragment has an associated label for later detection. The products of these four reactions are then separated with gel electrophoresis.

Sequencing methods, either enzymatic chain elongation reactions or chemical reactions, allow for base position determination and, therefore, DNA sequence determination. A sequencing instrument identifies the base from the specific emission wavelength corresponding to the four different ddNTPs or primers that are labeled with different fluorescent moieties that have a specific emission spectrum. Microorganisms can be identified though the DNA sequence, since the genomic information of particular loci is unique to individual species of microorganism.

For primer labeled enzymatic chain elongation reactions and chemical sequencing methods, four reactions for each dye labeled primers are required. After electrophoresis separation and fluorescence detection, four lanes of bands or peaks are observed as shown in FIG. 1A. A distinct color can represent each type of nucleotide. One can perform base calling by determining the band position in all four lanes to assign the sequence. For example as shown in FIG. 1A, the assign sequence could be CTTGATCTTCATGGTAGGC-CTCCTGAATCCT (Referred to herein as SEQ ID NO: 1). In addition, one can pool all four reaction solutions together to perform a single electrophoresis separation and obtain a single lane electropherogram containing all base information as shown in FIG. 1B. One could then call the DNA sequence by identifying the colors in order. If dye labeled terminators are used for the enzymatic chain elongation/termination reaction, the separation signals contain information concerning all the bases, as shown in FIG. 1B.

FIG. 2 represents a signal outcome from a DNA sequencing instrument wherein dye terminators are used for enzymatic chain elongation/termination reaction and all four reactions of primer labeled for enzymatic chain elongation reaction are pooled together. At any position, the highest color peak represents one of the nucleotides.

SUMMARY OF THE INVENTION

Embodiments of the invention provide for nucleotide sequence profiling for sample identification, obtained by a method comprising one or more of the steps of extracting a nucleotide sequence template from the sample, performing nucleotide sequence amplification on the template (e.g., via PCR) to create an amplified sample, performing less than four nucleotide-specific chemical cleavage reactions on the amplified template to obtain nucleotide sequence fragments, performing size-based separation on the sample fragments, detecting the sample fragments' separation, generating a profile based on the detection, and comparing the profile to a data base for sample identification. Such a method is useful for efficiently identifying a sample such as a microorganism and/or gene.

DESCRIPTION OF THE DRAWINGS

FIG. 1A shows a prior art four lane electropherogram.

FIG. 1B shows a prior art single lane electropherogram.

FIG. 2 shows a prior art DNA sequencing instrument output.

FIG. 10 shows electropherograms in accordance with an embodiment of the invention discussed in Example 4.

DETAILED DESCRIPTION OF THE INVENTION

Figure 3:
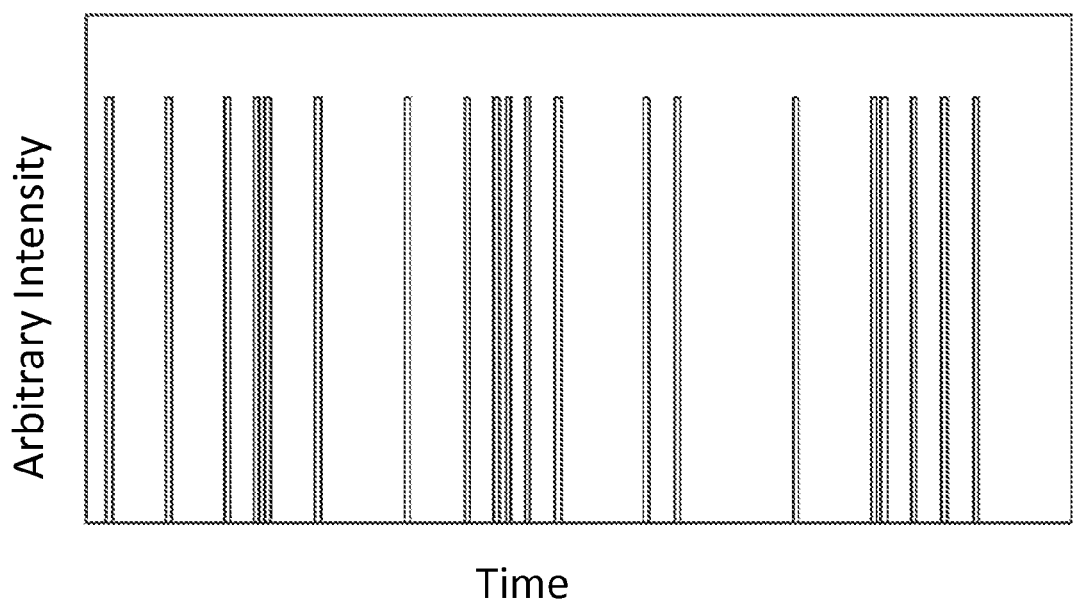
FIG. 3 shows a theoretical electropherogram for *Staphylococcus aureus* in accordance with an embodiment of the invention.

Embodiments of the invention include a method of profiling nucleotide sequences from a sample to identify the sample based on its genomic information without performing full DNA sequencing. Rather than full DNA sequencing, a profile may be generated based on the relative position of the nucleotide bases. The positions of one, two, or three of the four nucleotides are used to generate the profile, but not all four. If all four were used, then full DNA sequencing would have been performed. The profiling pattern of differentiating genetic elements can thereby be used to identify a sample of interest, without performing full DNA sequencing. The nucleotide sequence can be of any base length sufficient to provide a unique signature to the sample, and can include nucleic acids.

The accurate identification of a sample, such as a microorganism (e.g., bacteria, fungi, protozoans, algae, viruses) or a gene, is an important factor influencing appropriate therapy selection in disease diagnostics. Embodiments of the invention are useful to differentiate pathogenic microorganisms, aid in the selection of antimicrobial agents, and, in turn, decrease morbidity and mortality because of the application of more prompt and targeted therapy. Microorganism DNA can be extracted from patient samples such as blood, tissue, urine, etc. and used to determine the identification of the infecting microorganism with embodiments of the invention.

The accurate identification of certain genes and genetic mutations is also an important facture influencing therapy selection. For example, mutation in BRCA1 and BRCA2 genes significantly increase a person's risk of developing breast cancer. A mutation in a gene corresponds to a change in the DNA sequence, such as nucleotide(s) insertion, deletion, exchange, and/or base order change. Embodiments of the invention are useful for identifying these changes without performing full DNA sequencing of the sample. In accordance with embodiments of the invention, the gene can be amplified and cleaved, and a genetic profile is obtained. The genetic disorder can be identified by comparing the genetic profile to a reference library.

In many, if not most, instances, chemical cleavage reactions targeted to one of the four nucleotides will generate enough data to identify medically-important samples. For some organisms, cleavage reactions targeted at more than one nucleotide, but less than four, can be used to create the signature. A size-based separation and detection can then be performed. The pattern generated from the separation and detection can be used to identify the sample without going through base calling to identify the full DNA sequence.

Embodiments of the invention are useful for identifying any clinically relevant samples, such as microorganisms or other genetic organisms that provide nucleotide sequences, which in turn, provide nucleic acids, genes and other sequences. For example, Gram positive bacteria, Gram negative bacteria, fungi, yeasts, molds, and viruses, whether aerobic, anaerobic, or partial anaerobes, as well as in any form, such as cocci, rods, and spirochetes. Included also are microorganisms known or suspected of causing disease, such as enteric pathogens. Examples of such microorganisms include the genus *Corynebacterium, Actinomycetes, Streptomycetes, Nocardia, Enterobacter, Yersinia, Fancisella, Pasturella, Moraxella, Acinetobacter, Erysipelothrix, Branhamella, Actinobacillus, Streptobacillus, Listeria, alymmatobacterium, Brucella, Clostridium, Treponema, Escherichia, Salmonella, Kleibsiella, Vibrio, Proteus, Erwinia, Borrelia, Leptospira, Spirillum, Campylobacter, Shigella, Legionella, Pseudomonas, Aeromonas, Rickettsia, Chlamydia, Borrelia, Mycoplasma, Streptococcus* (e.g., Group A, B, C, D or *G. Streptococcus, S. pneumoniae, S. pyogenes, S. agalactiae, S. faecalis, S. faecium, S. durans*), *Neisseria* (e.g., *N. gonorrheae, N. meningitidis*), *Staphylococcus* (e.g., *S. aureus, S. epidermidis*), *Gardnerella, Mycobacterium* (e.g., *M. tuberculosis, M. bovis, M. ulcerans, M. leprae*), *Listeria, Bordetella* (e.g., *B. pertusis, B. parapertusis, B. bronchiseptica*), *Escherichia, Shigella, Haemophilus* (e.g., *H. influenzae, H. aegyptius, H. parainfluenzae, H. ducreyi*), *Salmonella, Citrobacter, Proteus* (e.g., *P. mirabilis, P. vulgaris, Yersinia, Kleibsiella, Serratia* (e.g., *S. marcessens, S. liquefaciens*), *Vibrio cholera, Shigella* (e.g., *S. dysenterii, S. flexneri*), *Pseudomonas aeruginosa, Franscisella tularensis, Brucella abortis, Bacillus* (e.g., *B. anthracis, B. cereus*), *Clostridium* (e.g., *C. perfringens, C. tetani, C. botulinum*), *Treponema, Rickettsia* and *Chlamydia*. These examples can be differentiated and identified, and characterized at the sub-species levels (i.e., strain typed), using methods in accordance with embodiments of the invention.

Performing chemical cleavage on DNA fragments obtained from an amplified template (e.g., PCR) provides a profiling pattern sufficient to identify a sample as long as the chemical digestion is reproducible. Accordingly, in some embodiments, DNA templates from samples of interest undergo PCR amplification before chemical cleavage. Typically, only one of the two primers is labeled with a fluorescent dye. As a result of single primer label, the resulting PCR product is labeled at one end of one of the DNA strands only. Any fragments after the chemical cleavage that still contain this fluorescent label can be detected with size-based separation (e.g., electrophoresis separation) and fluorescence detection. For example, consider a section of DNA from *Staphylococcus aureus* that has a sequence:

\*ATGTACCTGTAATCGCTGGTTCAGCATTAAAAGCTTTAGAAGGCGAT

GCTCAATATGAAGAAAAAATCTTAGAATTAATGGAAGCTGTAGATACT

TACAT (Referred to herein as (SEQ ID NO: 2)

\* represents the fluorescent dye label
Also consider the same section of DNA from *Staphylococcus epidermidis* which has a sequence:

\*ATGTACCTGTAATCGCTGGTTCTGCATTAAAAGCATTAGAAGGCGAT

GCTGAATACGAACAAAAAATCTTAGACTTAATGCAAGCAGTTGATGAT

TACAT (Referred to herein as SEQ ID NO: 3)

\* represents the fluorescent dye label.

The comparison of these sequences demonstrates that if one performed a full DNA sequence on this section of the genome from these bacteria, then the 10 base mismatches (underlined) could be used to differentiate these microorganisms. In this example, it is clear that a full DNA sequence is not necessary for this differentiation, but rather just the identification of the position of these nucleotide differences. Therefore, if one performed a chemical cleavage on one of the nucleotides, such as at the G position, one would obtain two DNA fragments for each G position for the above sequence section of *Staphylococcus aureus*. The following demonstrates the DNA fragments with dye labels that would be obtained if a cleavage reaction was performed on each of the G positions. The number in parentheses at the end of each sequence indicates the cleaved nucleotide base position. The fragment generated is detected based on the 5' fluorescent label (\*). The respective 3' fragment generated by cleavage would not be detected, since it does not contain a fluorescent label:

1) \*ATGTACCTGTAATCGCTGGTTCAGCATTAAAAGCTTTAGAAG
GCGATGCTCAATATGAAGAAAAAATCTTAGAATTAATGGAAGC
TGTA(G)(90)
(Referred to herein as SEQ ID NO: 4)

2) \*ATGTACCTGTAATCGCTGGTTCAGCATTAAAAGCTTTAGAAG
GCGATGCTCAATATGAAGAAAAAATCTTAGAATTAATGGAAGC
T(G)(87)
(Referred to herein as SEQ ID NO: 5)

3) \*ATGTACCTGTAATCGCTGGTTCAGCATTAAAAGCTTTAGAAG
GCGATGCTCAATATGAAGAAAAAATCTTAGAATTAATGGAA
(G)(84)
(Referred to herein as SEQ ID NO: 6)

4) \*ATGTACCTGTAATCGCTGGTTCAGCATTAAAAGCTTTAGAAG
GCGATGCTCAATATGAAGAAAAAATCTTAGAATTAATG(G)
(81)
(Referred to herein as SEQ ID NO: 7)

5) \*ATGTACCTGTAATCGCTGGTTCAGCATTAAAAGCTTTAGAAG
GCGATGCTCAATATGAAGAAAAAATCTTAGAATTAAT(G)
(80)
(Referred to herein as SEQ ID NO: 8)

6) \*ATGTACCTGTAATCGCTGGTTCAGCATTAAAAGCTTTAGAAG
GCGATGCTCAATATGAAGAAAAAATCTTA(G)(72)
(Referred to herein as SEQ ID NO: 9)

7) \*ATGTACCTGTAATCGCTGGTTCAGCATTAAAAGCTTTAGAAG
GCGATGCTCAATATGAA(G)(60)
(Referred to herein as SEQ ID NO: 10)

8) \*ATGTACCTGTAATCGCTGGTTCAGCATTAAAAGCTTTAGAAG
GCGATGCTCAATAT(G)(57)
(Referred to herein as SEQ ID NO: 11)

9) \*ATGTACCTGTAATCGCTGGTTCAGCATTAAAAGCTTTAGAAG
GCGAT(G)(48)
(Referred to herein as SEQ ID NO: 12)

10) \*ATGTACCTGTAATCGCTGGTTCAGCATTAAAAGCTTTAGAAG
GC(G)(45)
(Referred to herein as SEQ ID NO: 13)

11) \*ATGTACCTGTAATCGCTGGTTCAGCATTAAAAGCTTTAGAAG
(G)(43)
(Referred to herein as SEQ ID NO: 14)

12) \*ATGTACCTGTAATCGCTGGTTCAGCATTAAAAGCTTTAGAA
(G)(42)
(Referred to herein as SEQ ID NO: 15)

13) \*ATGTACCTGTAATCGCTGGTTCAGCATTAAAAGCTTTA(G)
(39)
(Referred to herein as SEQ ID NO: 16)

14) \*ATGTACCTGTAATCGCTGGTTCAGCATTAAAA(G)(33)
(Referred to herein as SEQ ID NO: 17)

15) \*ATGTACCTGTAATCGCTGGTTCA(G)(24)
(Referred to herein as SEQ ID NO: 18)

16) \*ATGTACCTGTAATCGCTG(G)(19)
(Referred to herein as SEQ ID NO: 19)

17) \*ATGTACCTGTAATCGCT(G)(18)
(Referred to herein as SEQ ID NO: 20)

18) \*ATGTACCTGTAATC(G)(15)
(Referred to herein as SEQ ID NO: 21)

19) \*ATGTACCT(G)(9)
(Referred to herein as SEQ ID NO: 22)

20) \*AT(G)(3)
(Referred to herein as SEQ ID NO: 23)

The cleavage at the G position of the amplicon generated for *Staphylococcus epidermidis* yields the following fragments:

1) \*ATGTACCTGTAATCGCTGGTTCTGCATTAAAAGCATTAGAAG
GCGATGCTGAATACGAACAAAAAATCTTAGACTTAATGCAAGC
AGTTGAT(G)(93)
(Referred to herein as SEQ ID NO: 24)

2) \*ATGTACCTGTAATCGCTGGTTCTGCATTAAAAGCATTAGAAG
GCGATGCTGAATACGAACAAAAAATCTTAGACTTAATGCAAGC
AGTT(G)(90)
(Referred to herein as SEQ ID NO: 25)

3) \*ATGTACCTGTAATCGCTGGTTCTGCATTAAAAGCATTAGAAG
GCGATGCTGAATACGAACAAAAAATCTTAGACTTAATGCAAGC
A(G)(87)
(Referred to herein as SEQ ID NO: 26)

4) \*ATGTACCTGTAATCGCTGGTTCTGCATTAAAAGCATTAGAAG
GCGATGCTGAATACGAACAAAAAATCTTAGACTTAATGCAA
(G)(84)
(Referred to herein as SEQ ID NO: 27)

5) \*ATGTACCTGTAATCGCTGGTTCTGCATTAAAAGCATTAGAAG
GCGATGCTGAATACGAACAAAAAATCTTAGACTTAAT(G)
(80)
(Referred to herein as SEQ ID NO: 28)

6) \*ATGTACCTGTAATCGCTGGTTCTGCATTAAAAGCATTAGAAG
GCGATGCTGAATACGAACAAAAAATCTTA(G)(72)
(Referred to herein as SEQ ID NO: 29)

7) \*ATGTACCTGTAATCGCTGGTTCTGCATTAAAAGCATTAGAAG
GCGATGCTGAATAC(G)(57)
(Referred to herein as SEQ ID NO: 30)

8) *ATGTACCTGTAATCGGTGGTTCTGCATTAAAAGCATTAGAAG
GCGATGCT(G) (51)
(Referred to herein as SEQ ID NO: 31)

9) *ATGTACCTGTAATCGCTGGTTCTGCATTAAAAGCATTAGAAG
GCGAT(G) (48)
(Referred to herein as SEQ ID NO: 32)

10) *ATGTACCTGTAATCGCTGGTTCTGCATTAAAAGCATTAGAAG
GC(G) (45)
(Referred to herein as SEQ ID NO: 33)

11) *ATGTACCTGTAATCGCTGGTTCTGCATTAAAAGCATTAGAAG
(G) (43)
(Referred to herein as SEQ ID NO: 34)

12) *ATGTACCTGTAATCGCTGGTTCTGCATTAAAAGCATTAGAA
(G) (42)
(Referred to herein as SEQ ID NO: 35)

13) *ATGTACCTGTAATCGCTGGTTCTGCATTAAAAGCATTA(G)
(39)
(Referred to herein as SEQ ID NO: 36)

14) *ATGTACCTGTAATCGCTGGTTCTGCATTAAAA(G) (33)
(Referred to herein as SEQ ID NO: 37)

15) *ATGTACCTGTAATCGCTGGTT(G) (24)
(Referred to herein as SEQ ID NO: 38)

16) *ATGTACCTGTAATCGCTG(G) (19)
(Referred to herein as SEQ ID NO: 39)

17) *ATGTACCTGTAATCGCT(G) (18)
(Referred to herein as SEQ ID NO: 40)

18) *ATGTACCTGTAATC(G) (15)
(Referred to herein as SEQ ID NO: 41)

19) *ATGTACCT(G) (9)
(Referred to herein as SEQ ID NO: 42)

20) *AT(G) (3)

Figure 4:
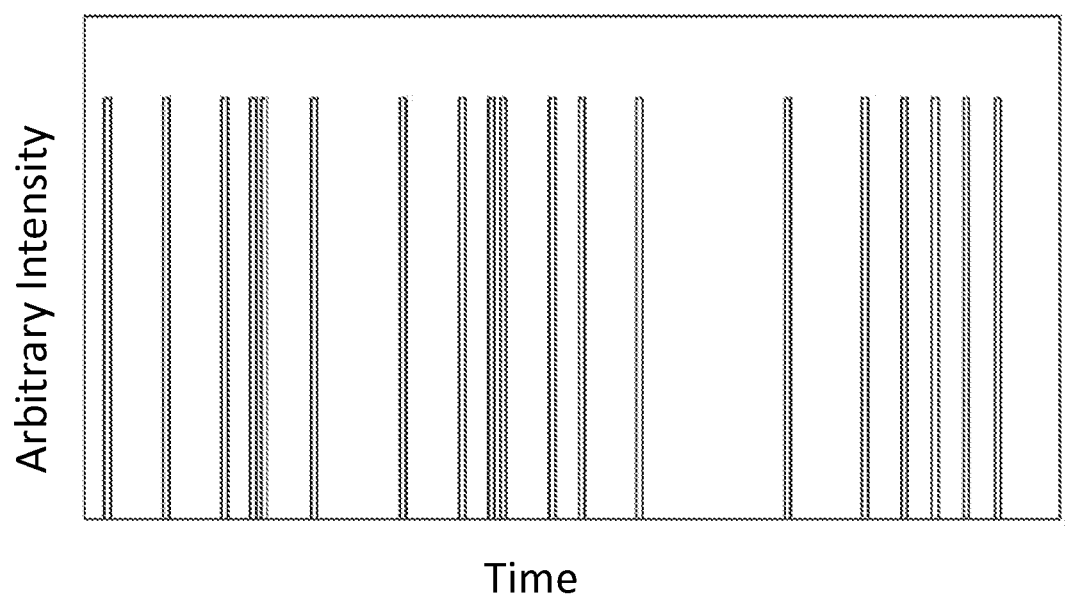
FIG. 4 shows a theoretical electropherogram for *Staphylococcus epidermidis* in accordance with an embodiment of the invention.

The performance of electrophoresis for size-based separation on the above fragments will result in the hypothetical electropherograms shown in FIG. 3 for *Staphylococcus aureus* and FIG. 4 for *Staphylococcus epidermidis*. It should be noted that *Staphylococcus aureus* has fragments with base lengths of 60 and 81 nucleotides in length that are not present in *S. epidermidis* (FIG. 4). Similarly, *S. epidermidis* has fragments with base lengths 93 and 84 nucleotides, which are not present in *S. aureus* (FIG. 3). These results indicate that one can use a chemical digestion reaction to identify microorganisms even to the species level based on the relative position and positional differences in single nucleotides. In addition, greater discrimination could be achieved by cleaving at additional bases without performing a full DNA sequence of a genome section. In some embodiments, additional base cleavage can be performed if cleavage at a single base does not provide sufficient information to definitively identify the sample.

Some embodiments of the invention provide for nucleotide sequence profiling for sample identification, obtained by a method comprising one or more of the following steps:

a) Obtaining a Nucleotide Sequence Template from a Sample.

A nucleotide sequence (e.g., DNA) template from a sample of interest can be obtained by any suitable method. For example, if the target is a microorganism presented in a culture (e.g., blood culture), sufficient nucleotide sequences may be obtained by performing a simple lysis reaction. This may be done through mechanical cellular disruption (e.g., bead and/or ultrasonication), chemical methods (e.g., sodium hydroxide lysis), thermal disruption, or a combination of these methods. If a microorganism is sought directly from a clinical specimen (i.e., a complex matrix) wherein limited copy numbers are present, then a nucleotide sequence extraction procedure may be necessary. For example, a solid phase extraction method can be used in which the DNA binds to a solid phase bead or column depending on the pH and buffer used. The bead or column can then be washed to remove any impurities. An elution buffer can be used to remove the DNA from the solid phase surface and the eluted DNA can be collected for future analysis.

b) Performing Amplification on the Template.

The template can be amplified using any suitable method. For example, PCR can be performed on the template using broad-range primers that are designed to amplify a genomic region that contains sufficient genetic variability to afford sample identification. The broad range primers may be the so-called "universal" primers, which will amplify any sample, such as a microorganism, in a large group (e.g., pan-fungal primers) or they may be for a select subset of microorganisms (e.g., the staphylococci). Regardless of the design, these primers function in the PCR to amplify a particular section of genomic nucleotide sequence (e.g., DNA) in which there is species-specific information. One of the primers in the pair is labeled with a dye for later DNA cleavage fragment identification; or both primers are labeled with different dyes for later DNA cleavage fragment identification. As an alternative, primers without dye labeled could be used to perform PCR and a derivative reaction could be performed on the PCR product to label one or both DNA chain(s). Also, labeled nucleotides could be used.

There are many universal primers useful for fungal or bacteria PCR reactions. For example, P1/P2, U1/U2, or ITS1/ITS4, etc. have been described for broad-range fungal PCR reactions. For bacteria PCR reaction, P11P/P13P, or Bac2F/Bac2R, etc, have been used for broad-range amplification.

c) Performing Chemical Cleavage on the Products Obtained in Step b), In Such a Way that Only One of the Four Nucleotides is Cut.

Chemicals can be used to selectively modify and cleave the nucleotide sequence strands (e.g., DNA) at A, G, T, or C. Use of limiting concentrations of such chemicals allows partial digestion of the DNA at different base positions.

There are many possible base specific cleavage reactions that can be used to cleave nucleotide sequences. For example, see Franca et al. "A Review of DNA Sequencing Techniques", Quarterly Rev. Biophy., 2002, Vol. 35, pp. 169-200, the relevant contents of which are hereby incorporated by reference. Piperidine, Pyrrolidine, NaOH, Hydrazine, $KMnO_4$, or formamide are specific examples of cleavage agents useful to break modified or non-modified nucleotide sequences at elevated temperatures.

d) Or, Alternatively, Performing Chemical Cleavage on the Products Obtained in Step b) at Multiple Nucleotide Positions.

Alternatively, chemicals can be used to selectively modify and cleave the DNA strands at more than 1, but less than 4, (i.e., two or three) nucleotide positions.

e) Performing Size-Based Separation on the Products Obtained in Step c) or d).

Size-based separation can be used to separate the product. Any useful method can be used. For example, electrophoresis can be used to separate the digested nucleotide sequence fragments based on their sizes. Examples include slab gel electrophoresis, capillary gel electrophoresis, multiplexed capillary gel electrophoresis, and microchip based gel electrophoresis. In some embodiments, electrophoresis instruments such as the DNA PROFiler or cePRO 9600 F1, available from Advanced Analytical Technologies, Inc., Ames, Iowa, assignee of the present application, can be used for the size-based separation step.

f) Detecting the Products after Step e) Separation.

After size-based separation, the cleavage products can be detected by a fluorescent signal in embodiments where digested nucleotide sequence fragments contain a dye label. Many dyes can be used to label the primers, such as any dye useful for nucleotide sequencing, such as FAM, JOE, TAMRA, ROX, and energy transfer dyes.

g) Generating a Profile Based on the Detection in Step f).

Figure 5:
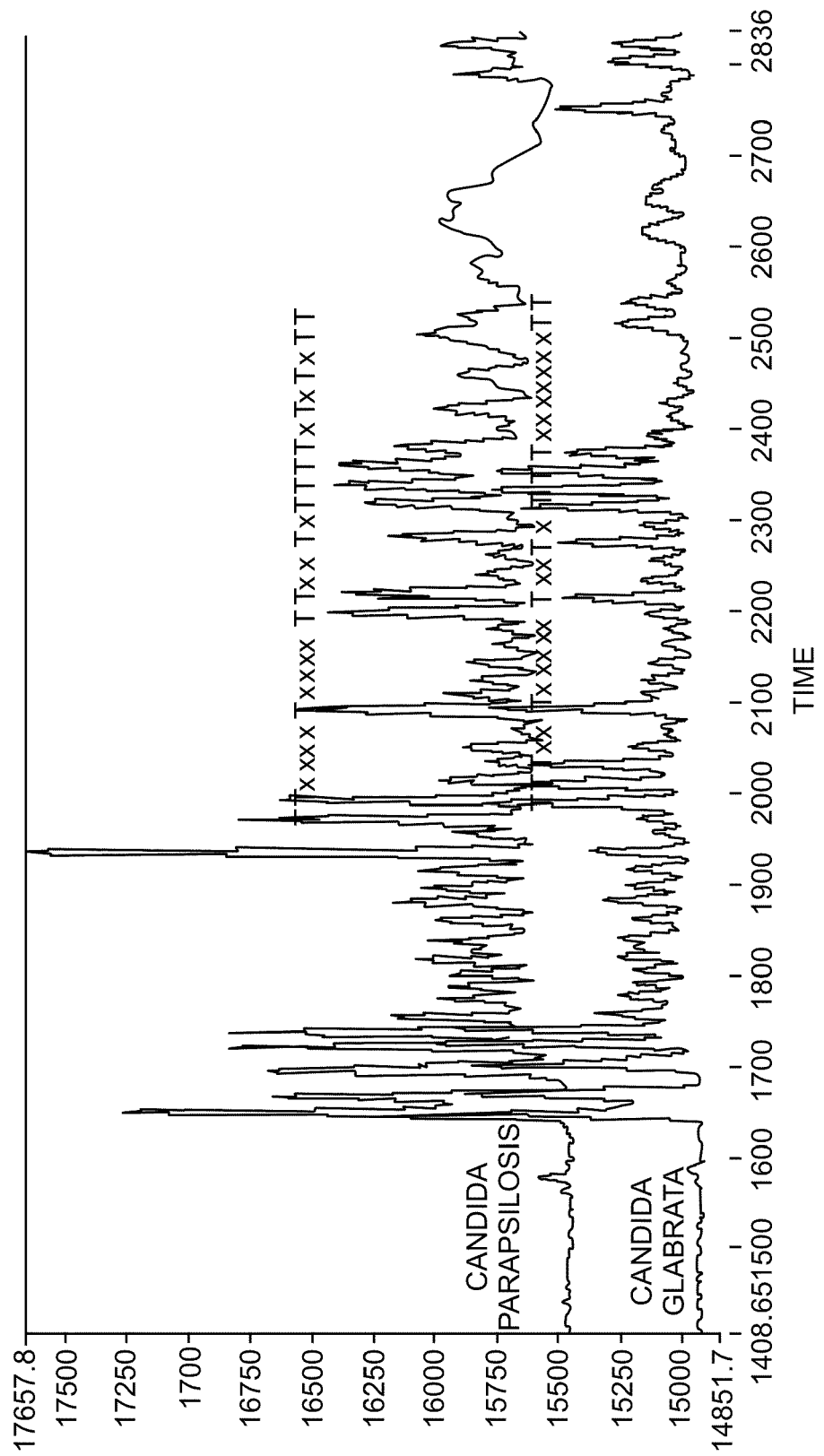
FIG. 5 shows an electropherogram in accordance with an embodiment of the invention discussed in Example 1.

A profile, such as the profile shown in FIG. 5, can be generated. Once the electropherograms are generated from the samples, one can extract the peak positions, and/or peak heights, and/or peak widths from each electropherogram to form the basic information for the nucleotide sequence profile.

h) Comparing the Profile Generated in Step g) to the Data Base for Sample Identification.

The created profile can be compared to a data base to identify the sample. A comparison algorithm can be used to compare the sample profile to a database for sample identification.

After the nucleotide sequence profile is generated, the profile is compared to a known database to identify the sample. Any pattern recognition algorithm useful for comparing the nucleotide sequence profile to the database can be used. For example, the migration time of each peak identified in the electropherogram can be used to compare the pattern with the use of principle components analysis. See Duarte et al. "Application of Chemometrics in Separation Science", J. Liq. Chromatogr. & Related Tech., 2006, Vol. 29, pp. 1143-1176, the relevant contents of which are hereby incorporated by reference. As another example, dynamic programming to align sample electropherogram to a standard electropherogram may be used. See Guillo et al. "Micellar Electrokinetic Capillary Chromatography And Data Alignment Analysis: A New Tool In Urine Profiling", J. Chromatogr. A, 2004, Vol. 1027, pp. 203-212, the relevant contents of which are hereby incorporated by reference. Such an approach uses dynamic programming to correct the migration time shifts and to provide a similarity score between whole electropherograms. Another approach uses the peak height information in the coded sequences to improve the reliability of the searching algorithm. See Ceballos et al. "Pattern Recognition In Capillary Electrophoresis Data Using Dynamic Programming In The Wavelet Domain", Electrophoresis, 2008, Vol. 29, pp. 2828-2840, the relevant contents of which are hereby incorporated by reference.

Figure 6:
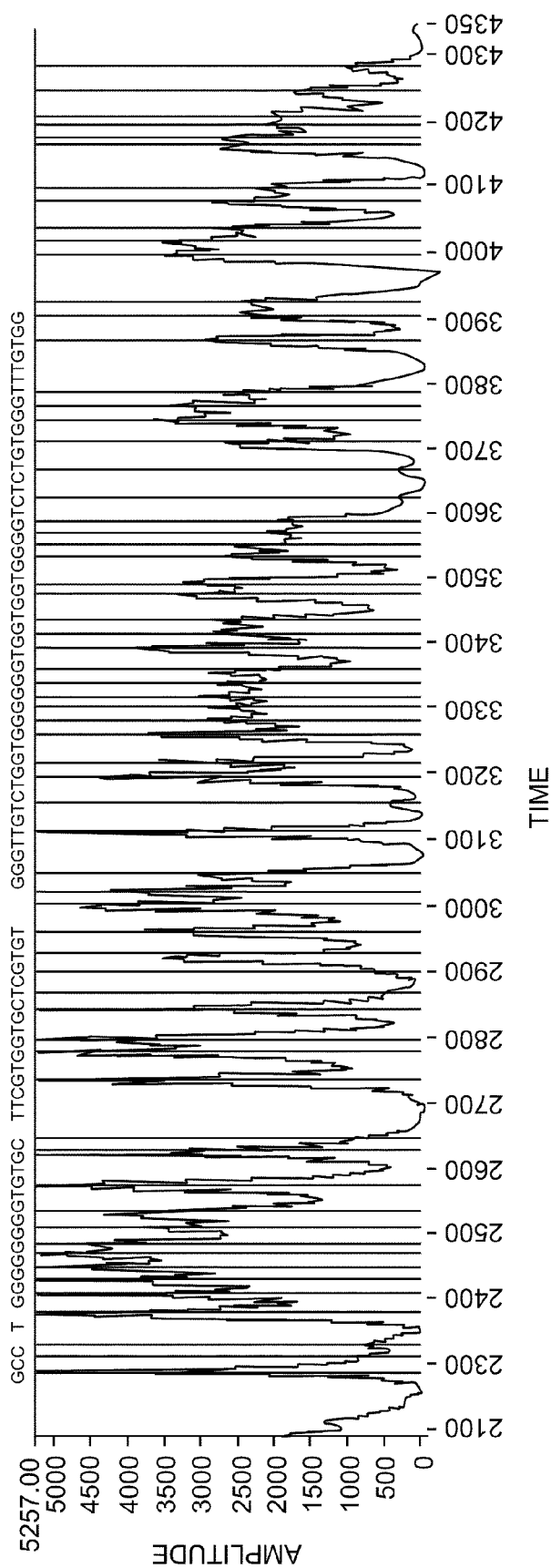
FIG. 6 shows the conversion result of electropherogram into character coding in accordance with an embodiment of the invention.

Generally, the following proposed method can be used to perform pattern recognition without the complication of performing correction of the migration time:

1. The electropherogram may be smoothed first to reduce noise. Algorithms such as moving average, wavelet, FFT, or Savitzky-Golay filters can be used to smooth out the data to reduce noise.
2. The peaks of the electropherogram are identified, as shown in FIG. 6 with vertical lines. First and second derivatives can be used to identify each peak position.
3. The peaks are divided into groups depending on their intensities. For example, FIG. 6 marks the larger intensity peaks as G while smaller peaks as C.
4. The spacing between adjacent identified peaks is calculated. A distribution or histogram from the spacing values can be created. A gap threshold can then be estimated to determine the standard peak spacing between adjacent peaks. When the adjacent peak spacing is, for example, two times larger than the threshold, a gap can be identified and marked as T, as shown in FIG. 6. When the adjacent peaks spacing is, for example, three times larger than the threshold, then the gap can be identified and marked with two Ts, and so on.

With such a method, electropherograms from a reference database and an unknown sample are transformed from an analogue signal to character coding. For example, the electropherogram in FIG. 6 transformed into character coding by using the previous described method produces the following result:

GCCTGGGGGGGGTGTGCTTCGTGGTGCTCGTGTGGGTTGTCTGGTGGG

GGGTGGGTGGTGGGGTCTCTGTGGGTTTGTGGTTGGGTGGTTGGGGTG

TG

Where G represents the peaks larger than a threshold while C represents the peaks smaller than the threshold and T represents a gap.

Figure 7:
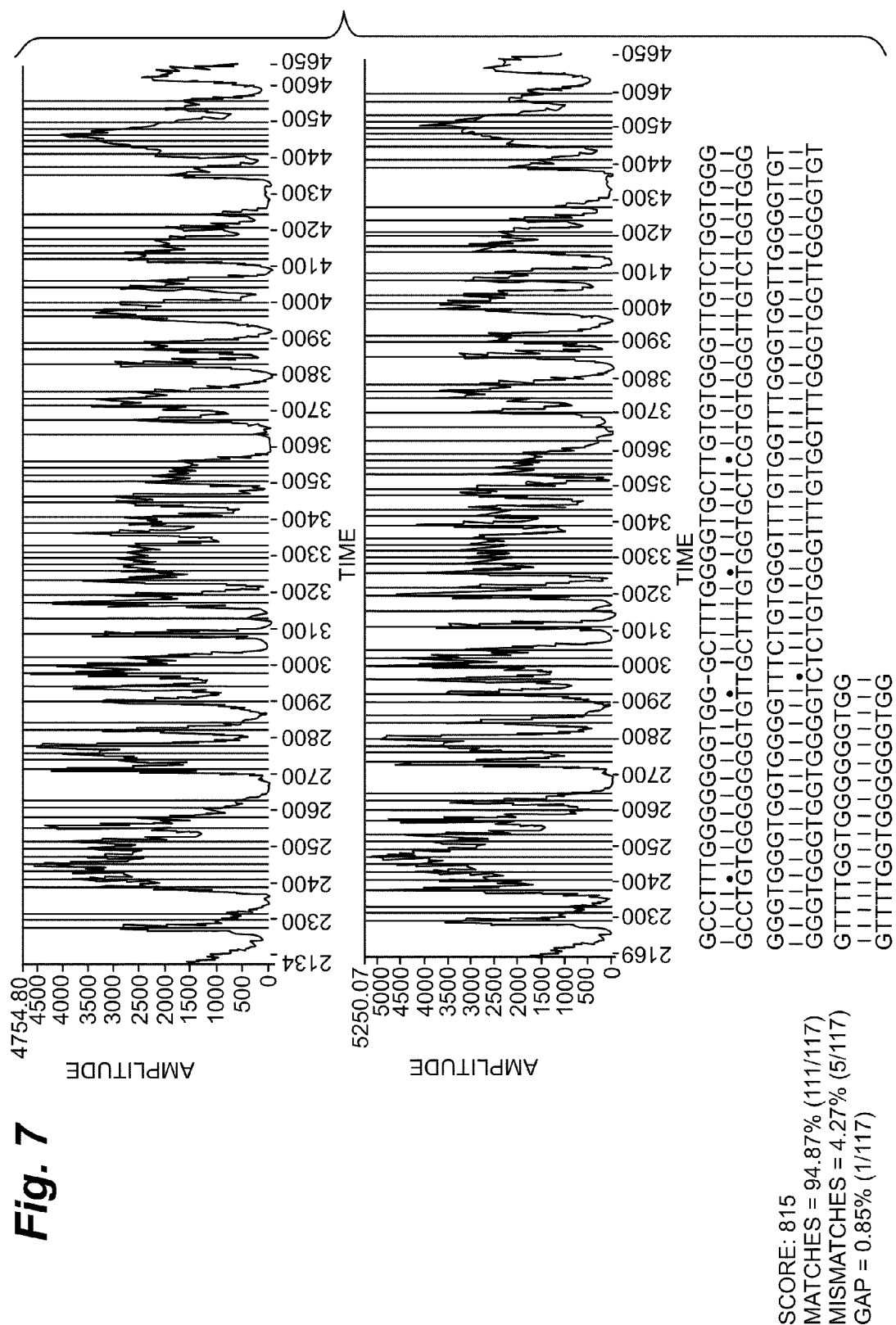
FIG. 7 shows a comparison result of using character coding and pair-wise alignment in accordance with an embodiment of the invention.

A pair-wise alignment algorithm, such as Needleman-Wunsch global alignment or Smith-Waterman local alignment, can then be used to compare the character codings from the sample electropherogram to the database reference electropherogram. Such a method can be used to determine the difference between the electropherograms, as shown in FIG. 7.

Accordingly, embodiments of invention use the pattern generated from cleaved nucleotide sequence fragments to form a fingerprint for sample identification. With such a method, there is no need to identify individual fragments for nucleotide base calling as in full DNA sequencing.

EXAMPLES

The examples below are merely illustrative and are not intended to limit the scope of the invention.

Example 1

Generating a DNA Profile Through a Chemical Cleavage Performed on One of the Four Nucleotide Positions DNA templates from *Candida* species: *C. parapsilosis* and *C. glabrata* were extracted and PCR was performed with universal primer pair U1/U2. U1 was labeled with the fluorescent dye fluorescein. U1 is a forward primer having the following sequence: GTGAAATTGT TGAAAGGGAA. (Referred to herein as SEQ ID NO: 43). U2 is a reverse primer having the following sequence: GACTCCTTGGTCCGT-GTT. (Referred to herein as SEQ ID NO: 44). When these two primers are used for PCR on these *Candida* species, a ~260 base pair amplicon is created for each specie. The products from PCR were purified through spin column or ethanol precipitation before chemical cleavage. 50 µl of DNA solution was preheated to 95° C. for 3-5 minutes before adding 7.77 µl of 0.5 mM $KMnO_4$. Then 6 µl of 1.1 M pyrrolidine was added directly to the reaction mixtures and these were maintained at 90° C. for 20 minutes. After the reaction, 1 ml of butanol was added to the reaction mixtures, which were then vortexed and spun to separate the organic phase from the aqueous phase. The top organic phase was removed and discarded. Another 1 ml butanol with 0.1% SDS was added into the remaining aqueous phase and spun for 5 minutes to precipitate the DNA. The DNA pellets were rinsed with 70% ethanol and re-suspended in 50 μl of a water formamide mixture. The final solution was heated at 95° C. for 3 minutes before being analyzed with a capillary electrophoresis system with fluorescence detection. FIG. 5 shows the overlay of the two electropherograms. This reaction mainly cleaves at thymine (T) base positions. There are total of six T nucleotides mismatches between these two species in this region. Therefore, the two species may be differentiated and identified by comparing their partial DNA profiling without knowing the full DNA profile for the section of genome. In addition, one could search a database, in which includes the DNA profiles of all desired microorganisms with the same chemical digestion method, to match an unknown profile to the database for identification.

Example 2

Figure 8:
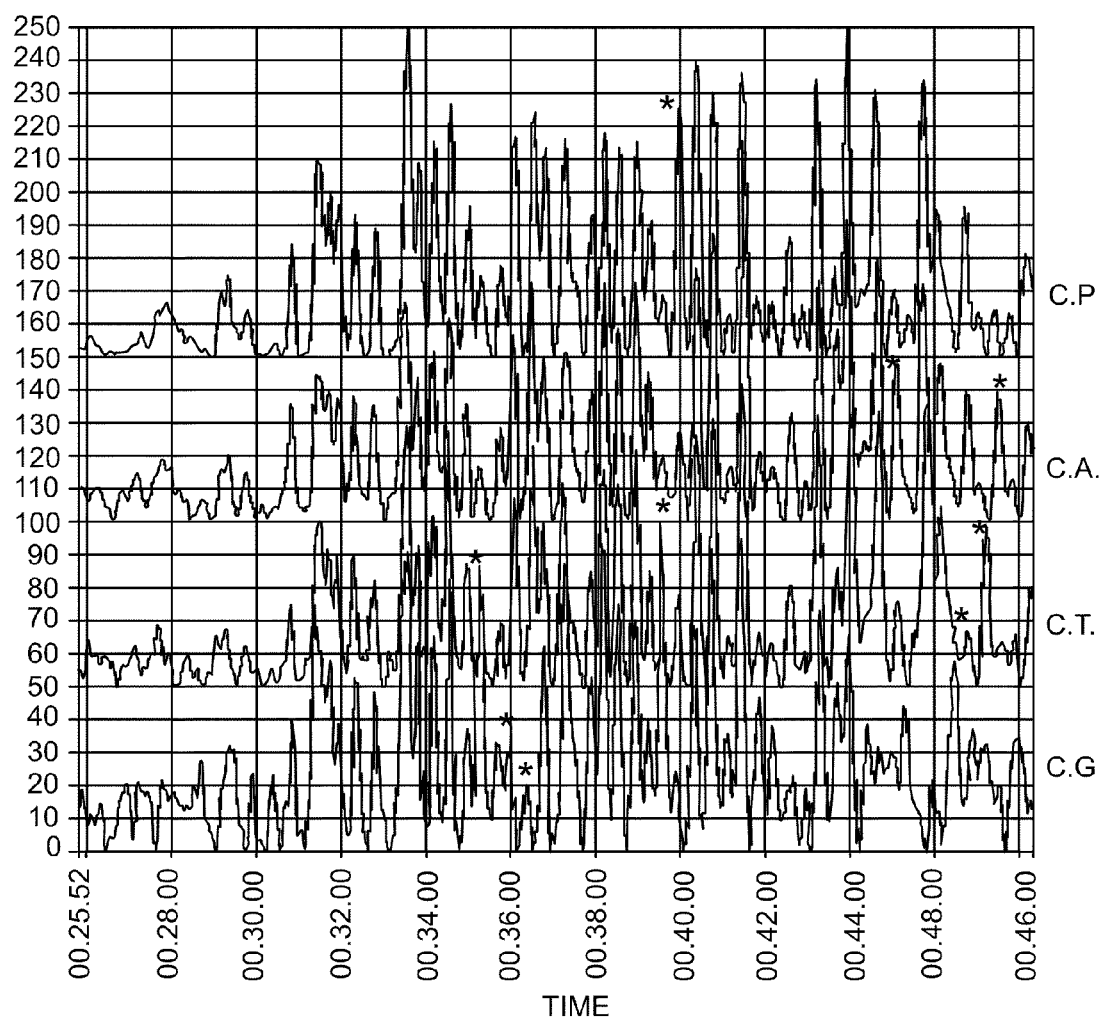
FIG. 8 shows an electropherogram in accordance with an embodiment of the invention discussed in Example 2.

Generating a DNA Profile Through a Chemical Cleavage Method on Multiple Base Positions DNA templates from *Candida* species: *C. parapsilosis, C. glabrata, C. albicans*, and *C. tropicalis* were used for PCR with a universal primer as described in Example 1. The DNA were modified and digested with N-dimethylformamide and 3 mM $MnCl_2$ at 110° C. for 30 minutes. The same method described in Example 1 for sample purification was used before sample injection and electrophoresis separation. FIG. 8 shows the electropherograms for each of the samples. For a 5'-end-labeled DNA fragment, each random degradation creates two fragments that contained the labeled dye. See Negri et al. "One-Step, One-Lane Chemical DNA Sequencing by N-Methylformamide in the Presence of Metal Ions", Bio-Tech., 1996, Vol. 21, pp. 910-917, the relevant contents of which are hereby incorporated by reference. Although N-dimethylformamide cuts at the 5' and 3' positions on the sugar base, the 5' cleavage is less efficient. Two fragments that contain dye label are generated while one has one more sugar base than the other. Two visible bands for each DNA strand were generated. This is not desirable for DNA sequencing because of the mixed signals. However, for DNA profiling, the actual cleavage position is not important as long as it is reproducible. As shown in FIG. 8, one can distinguish the four Candida species from each other.

Example 3

Figure 9:
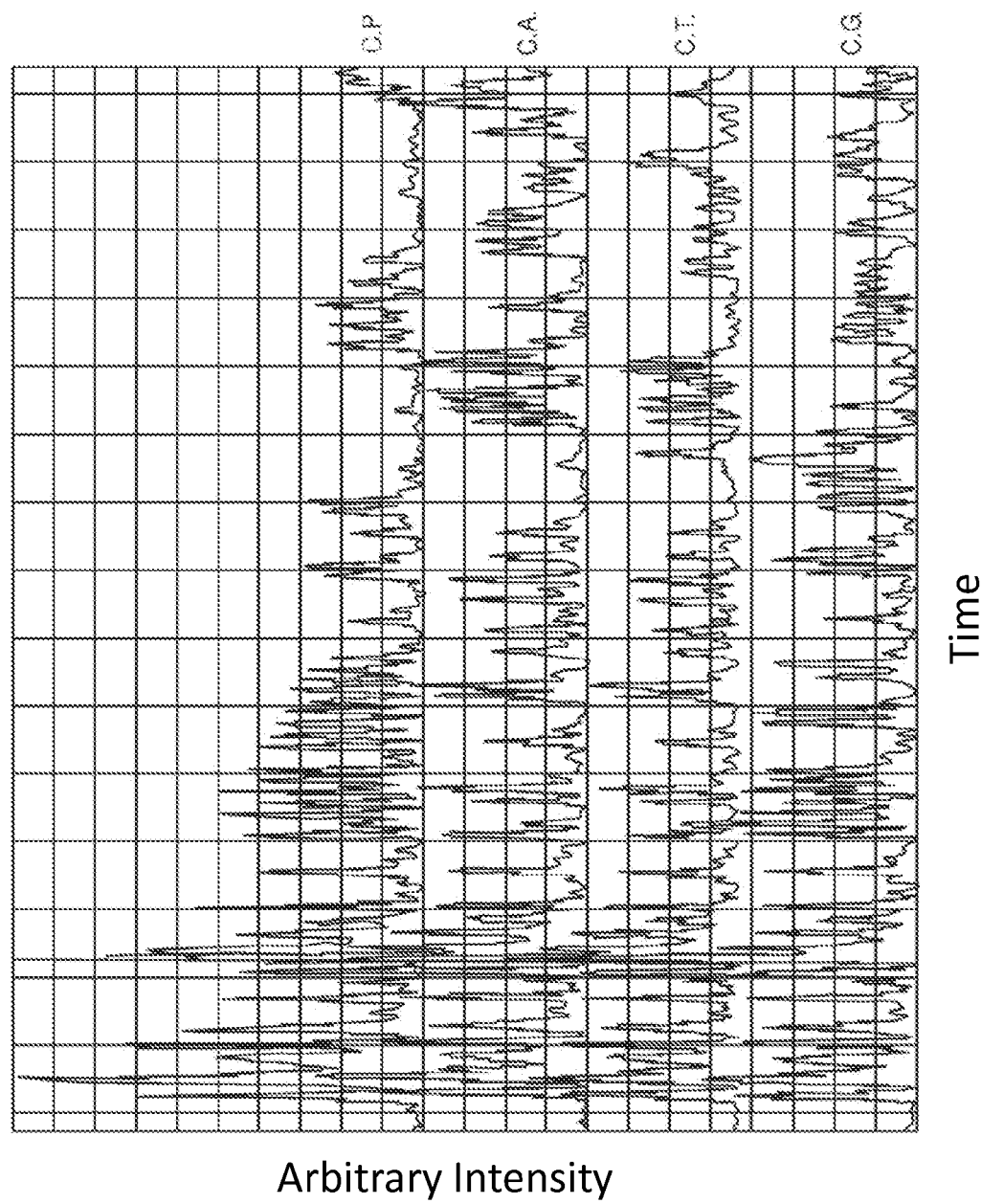
FIG. 9 shows an electropherogram in accordance with an embodiment of the invention discussed in Example 3.

Generating a DNA Profile Through a Chemical Cleavage Method on Multiple Base Positions DNA templates from *Candida* species: *C. parapsilosis, C. glabrata, C. albicans*, and *C. tropicalis* were used for PCR with universal primer pair ITS1/ITS4. ITS1 was labeled with the fluorescent dye fluorescein. ITS1 is a forward primer having the following sequence: TCCGTAGGTGAACCT-GCGG. (Referred to herein as SEQ ID NO: 45). ITS4 is a reverse primer having the following sequence: GCATAT-CAATAAGCGGAGGA. (Referred to herein as SEQ ID NO: 46). When these two primers are used for PCR on these Candida species, a ~580 base pair amplicon is created for each specie. After purification of the PCR product, 80% of N-methylformamide was used to cleave the DNA at 110° C. for 30 minutes. The samples were then separated with electrophoresis without further purification as in Examples 1 and 2. FIG. 9 shows the electropherograms for each of the cleavage samples. This reaction preferably cleaves DNA at the G and A positions with moderate cleavage at the C position and insignificant cleavage at the T position. From FIG. 9, one can identify the difference between these species.

Example 4

In previous examples, only one primer was labeled with a fluorescent dye for later profiling detection. Since only one primer was labeled, the fragments that come from the strand containing the labeled primer were detected on the separation system after the chemical digestion. However, one could also label both primers with different dyes. For example, in Example 3 the forward primer IST1 could be labeled with FAM (carboxyfluorescein), which has a maximum emission at ~520 nm and the reverse primer IST4 labeled with Cy-5, which has a maximum emission at ~670 nm. The fluorescent signals generated would then come from both dye labels. If the fluorescence detection system is capable of identifying the different emission wavelength, then the two signals could separate from one another. For example, if the detection system examines two wavelength bands, one centrals at 520 nm with bandwidth ±40 nm and the other centrals at 670 nm±40 nm, then one could determine which fragments came from which strand of DNA. Then, the electropherograms could be re-constructed according to the emission wavelength, i.e., one electropherogram shows the fragments having emission at 520 nm and the other electropherogram shows the fragments having emission at 670 nm. Since both strands of DNA are complementary to each other, in this manner one could get twice the amount of information, which could be used to identify the microorganism, in contrast to generating a DNA profile from one end of the DNA alone.

For example, consider the Staphylococcus aureus tuf gene, which has the following DNA sequence:

5'-<u>TATTCTCAATCACTGGTCGT</u>GGTACTGTTGCTACAGGCCGTGTTG
AACGTGGTCAAA
(Referred to herein as SEQ ID NO: 47)

3'-<u>ATAAGAGTTAGTGACCAGCA</u>CCATGACAACGATGTCCGGCACAAC
TTGCACCAGTTT
(Referred to herein as SEQ ID NO: 48)

TCAAAGTTGGTGAAGAAGTTGAAATCATCGGTTTACATGACACATCTAA
AACAACTGTTAAGTTTCAACCACTTCTTCAACTTTAGTAGCCAAATGTA
CTGTGTAGATTTTGTTGACAAT
(Referred to herein as SEQ ID NO: 49)

CAGGTGTTGAAATGTTCCGTAAATTAT<u>TAGACTACGCTGAAGCT</u>-3'
(Referred to herein as SEQ ID NO: 50)

GTCCACAACTTTACAAGGCATTTAATA<u>ATCTGATGCGACTTCGA</u>-5'
(Referred to herein as SEQ ID NO: 51)

The following DNA sequence can be selected as primers for the PCR amplification:

5'-TATTCTCAATCACTGGTCGT-3' (Referred to herein as SEQ ID NO: 52)

5'-AGCTTCAGCGTAGTCTA-3'. (Referred to herein as SEQ ID NO: 53)

In addition, 5'-TATTCTCAATCACTGGTCGT-3' can be labeled with a fluorescence dye such as FAM in the 5' position and 5'-AGCTTCAGCGTAGTCTA-3' can be labeled with a fluorescence dye such as Cy-5 at the 5' position. After the PCR amplification for *Staphylococcus aureus* DNA, one strand of PCR product contains a green fluorescence dye while the other strand of DNA contains a red fluorescence dye. Accordingly, the double-stranded DNA can be labeled with different dyes for each strand of DNA and can be cleaved in the same cleavage reaction. After the cleavage reaction, a capillary electrophoresis with fluorescence detection system can be used to separate and differentiate the fragments that labeled with different dyes simultaneously. FIG. 10 shows the separation results. The bottom trace represents the blue emission wavelength from 480 nm to 560 nm and the top trace represents the red emission wavelength from 620 nm and up. The 480 nm to 560 nm represents the emission from FAM labeled DNA fragments while the other wavelength represents the emission from Cy-5 labeled DNA fragments. The traces have different patterns since each trace represents each DNA strand at the opposite direction. This two-color method allows better coverage of the PCR amplicons to reveal the more subtle change of the DNA sequences in between sub- species. If the fragments from one strand could not differentiate the microorganism, the fragments from the other strand may provide additional information for microorganism identification.

These examples show several embodiments of the invention in which DNA molecules produced from the PCR are chemically cleaved at a specific location(s). When these are separated, for example by electrophoresis, then a DNA profile is generated that is based on the DNA sequence. The DNA profile can be used to identify the microorganism species from a database. In addition, even if the DNA profile did not perfectly match an entry in the database, a "most likely match" or percent identity value could still be generated to indicate the possible species for the microorganism.

What is claimed is:

1. A method of sample identification, comprising the steps of obtaining at least one nucleotide sequence template from the sample, amplifying the nucleotide sequence template, performing only three nucleotide-specific chemical cleavage reactions on the amplified template to obtain nucleotide sequence fragments, performing size-based separation on the nucleotide sequence fragments, detecting the fragments' separation, generating a unique profile based on the detection, and comparing the profile to a data base to identify the sample.

2. The method of claim 1, wherein the size-based separation includes an electrophoresis separation.

3. The method of claim 2, wherein the detecting the size separation step includes detecting a fluorescent dye label associated with the fragments.

4. The method of claim 1, wherein the detecting the size separation step includes detecting a fluorescent dye label associated with the fragments.

5. The method of claim 4, wherein the profile is an electropherogram.

6. The method of claim 2, wherein the detecting the size separation step includes detecting two different dye labels associated with the fragments.

7. The method of claim 1 wherein the detecting the size separation step includes detecting two different fluorescent dye labels associated with the fragments.

8. The method of claim 7, wherein the profile is an electropherogram.

9. The method of claim 1, wherein the profile is an electropherogram.

10. The method of claim 1, wherein the amplification step includes PCR.

11. The method of claim 1, wherein the nucleotide sequence is DNA.

12. The method of claim 1, wherein the sample is a microorganism.

13. The method of claim 1, wherein the sample is a gene.

14. A method of microorganism identification, comprising the steps of obtaining at least one nucleotide sequence template from the microorganism, amplifying the nucleotide sequence template, performing only three nucleotide-specific chemical cleavage reactions on the amplified template to obtain nucleotide sequence fragments, performing size-based separation on the nucleotide sequence fragments, detecting the fragments' separation, generating a profile based on the detection, and comparing the profile to a data base to identify the microorganism.

15. A method of microorganism identification, comprising the steps of obtaining at least one nucleotide sequence template from the microorganism, amplifying of the template with PCR on the template, performing only three nucleotide-specific chemical cleavage reactions on the amplified template to obtain nucleotide sequence fragments, performing size-based separation on the fragments with an electrophoresis separation, detecting the product fragments' separation by detecting a fluorescent dye label associated with the product, generating an electropherogram based on the detection, and comparing the electropherogram to a data base to identify the microorganism.

* * * * *

```
                        SEQUENCE LISTING

<160> NUMBER OF SEQ ID NOS: 54

<210> SEQ ID NO 1
<211> LENGTH: 31
<212> TYPE: DNA
<213> ORGANISM: Unknown
<220> FEATURE:
<223> OTHER INFORMATION: chemically synthesized

<400> SEQUENCE: 1
cttgatcttc atggtaggcc tcctgaatcc t                              31

<210> SEQ ID NO 2
<211> LENGTH: 100
<212> TYPE: DNA
<213> ORGANISM: Staphylococcus aureus

<400> SEQUENCE: 2
atgtacctgt aatcgctggt tcagcattaa aagctttaga aggcgatgct caatatgaag    60
aaaaaatctt agaattaatg gaagctgtag atacttacat                         100

<210> SEQ ID NO 3
<211> LENGTH: 100
<212> TYPE: DNA
<213> ORGANISM: Staphylococcus epidermidis

<400> SEQUENCE: 3
atgtacctgt aatcgctggt tctgcattaa aagcattaga aggcgatgct gaatacgaac    60
aaaaaatctt agacttaatg caagcagttg atgattacat                         100

<210> SEQ ID NO 4
<211> LENGTH: 90
<212> TYPE: DNA
<213> ORGANISM: Staphylococcus aureus

<400> SEQUENCE: 4
atgtacctgt aatcgctggt tcagcattaa aagctttaga aggcgatgct caatatgaag    60
aaaaaatctt agaattaatg gaagctgtag                                    90

<210> SEQ ID NO 5
<211> LENGTH: 87
<212> TYPE: DNA
<213> ORGANISM: Staphylococcus aureus

<400> SEQUENCE: 5
atgtacctgt aatcgctggt tcagcattaa aagctttaga aggcgatgct caatatgaag    60
```

```
aaaaaatctt agaattaatg gaagctg                                              87

<210> SEQ ID NO 6
<211> LENGTH: 84
<212> TYPE: DNA
<213> ORGANISM: Staphylococcus aureus
<220> FEATURE:
<223> OTHER INFORMATION:

<400> SEQUENCE: 6
atgtacctgt aatcgctggt tcagcattaa aagctttaga aggcgatgct caatatgaag    60
aaaaaatctt agaattaatg gaag                                             84

<210> SEQ ID NO 7
<211> LENGTH: 81
<212> TYPE: DNA
<213> ORGANISM: Staphylococcus aureus

<400> SEQUENCE: 7
atgtacctgt aatcgctggt tcagcattaa aagctttaga aggcgatgct caatatgaag    60
aaaaaatctt agaattaatg g                                                81

<210> SEQ ID NO 8
<211> LENGTH: 80
<212> TYPE: DNA
<213> ORGANISM: Staphylococcus aureus

<400> SEQUENCE: 8
atgtacctgt aatcgctggt tcagcattaa aagctttaga aggcgatgct caatatgaag    60
aaaaaatctt agaattaatg                                                  80

<210> SEQ ID NO 9
<211> LENGTH: 72
<212> TYPE: DNA
<213> ORGANISM: Staphylococcus aureus

<400> SEQUENCE: 9
atgtacctgt aatcgctggt tcagcattaa aagctttaga aggcgatgct caatatgaag    60
aaaaaatctt ag                                                          72

<210> SEQ ID NO 10
<211> LENGTH: 60
<212> TYPE: DNA
<213> ORGANISM: Staphylococcus aureus

<400> SEQUENCE: 10
atgtacctgt aatcgctggt tcagcattaa aagctttaga aggcgatgct caatatgaag    60

<210> SEQ ID NO 11
<211> LENGTH: 57
<212> TYPE: DNA
<213> ORGANISM: Staphylococcus aureus

<400> SEQUENCE: 11
atgtacctgt aatcgctggt tcagcattaa aagctttaga aggcgatgct caatatg       57

<210> SEQ ID NO 12
<211> LENGTH: 48
<212> TYPE: DNA
<213> ORGANISM: Staphylococcus aureus

<400> SEQUENCE: 12
```

```
atgtacctgt aatcgctggt tcagcattaa aagctttaga aggcgatg         48
```

<210> SEQ ID NO 13
<211> LENGTH: 45
<212> TYPE: DNA
<213> ORGANISM: Staphylococcus aureus

<400> SEQUENCE: 13

```
atgtacctgt aatcgctggt tcagcattaa aagctttaga aggcg            45
```

<210> SEQ ID NO 14
<211> LENGTH: 43
<212> TYPE: DNA
<213> ORGANISM: Staphylococcus aureus

<400> SEQUENCE: 14

```
atgtacctgt aatcgctggt tcagcattaa aagctttaga agg              43
```

<210> SEQ ID NO 15
<211> LENGTH: 42
<212> TYPE: DNA
<213> ORGANISM: Staphylococcus aureus

<400> SEQUENCE: 15

```
atgtacctgt aatcgctggt tcagcattaa aagctttaga ag               42
```

<210> SEQ ID NO 16
<211> LENGTH: 39
<212> TYPE: DNA
<213> ORGANISM: Staphylococcus aureus

<400> SEQUENCE: 16

```
atgtacctgt aatcgctggt tcagcattaa aagctttag                   39
```

<210> SEQ ID NO 17
<211> LENGTH: 33
<212> TYPE: DNA
<213> ORGANISM: Staphylococcus aureus

<400> SEQUENCE: 17

```
atgtacctgt aatcgctggt tcagcattaa aag                         33
```

<210> SEQ ID NO 18
<211> LENGTH: 24
<212> TYPE: DNA
<213> ORGANISM: Staphylococcus aureus

<400> SEQUENCE: 18

```
atgtacctgt aatcgctggt tcag                                   24
```

<210> SEQ ID NO 19
<211> LENGTH: 19
<212> TYPE: DNA
<213> ORGANISM: Staphylococcus aureus

<400> SEQUENCE: 19

```
atgtacctgt aatcgctgg                                         19
```

<210> SEQ ID NO 20
<211> LENGTH: 18
<212> TYPE: DNA
<213> ORGANISM: Staphylococcus aureus

<400> SEQUENCE: 20

```
atgtacctgt aatcgctg                                                    18
```

<210> SEQ ID NO 21
<211> LENGTH: 15
<212> TYPE: DNA
<213> ORGANISM: Staphylococcus aureus

<400> SEQUENCE: 21

```
atgtacctgt aatcg                                                       15
```

<210> SEQ ID NO 22
<211> LENGTH: 9
<212> TYPE: DNA
<213> ORGANISM: Staphylococcus aureus

<400> SEQUENCE: 22

```
atgtacctg                                                               9
```

<210> SEQ ID NO 23
<211> LENGTH: 3
<212> TYPE: DNA
<213> ORGANISM: Staphylococcus aureus

<400> SEQUENCE: 23

```
atg                                                                     3
```

<210> SEQ ID NO 24
<211> LENGTH: 93
<212> TYPE: DNA
<213> ORGANISM: Staphylococcus epidermidis

<400> SEQUENCE: 24

```
atgtacctgt aatcgctggt tctgcattaa aagcattaga aggcgatgct gaatacgaac      60
aaaaaatctt agacttaatg caagcagttg atg                                   93
```

<210> SEQ ID NO 25
<211> LENGTH: 90
<212> TYPE: DNA
<213> ORGANISM: Staphylococcus epidermidis

<400> SEQUENCE: 25

```
atgtacctgt aatcgctggt tctgcattaa aagcattaga aggcgatgct gaatacgaac      60
aaaaaatctt agacttaatg caagcagttg                                       90
```

<210> SEQ ID NO 26
<211> LENGTH: 87
<212> TYPE: DNA
<213> ORGANISM: Staphylococcus epidermidis

<400> SEQUENCE: 26

```
atgtacctgt aatcgctggt tctgcattaa aagcattaga aggcgatgct gaatacgaac      60
aaaaaatctt agacttaatg caagcag                                          87
```

<210> SEQ ID NO 27
<211> LENGTH: 84
<212> TYPE: DNA
<213> ORGANISM: Staphylococcus epidermidis

<400> SEQUENCE: 27

```
atgtacctgt aatcgctggt tctgcattaa aagcattaga aggcgatgct gaatacgaac      60
aaaaaatctt agacttaatg caag                                             84
```

```
<210> SEQ ID NO 28
<211> LENGTH: 80
<212> TYPE: DNA
<213> ORGANISM: Staphylococcus epidermidis

<400> SEQUENCE: 28
atgtacctgt aatcgctggt tctgcattaa aagcattaga aggcgatgct gaatacgaac    60
aaaaaatctt agacttaatg                                                80

<210> SEQ ID NO 29
<211> LENGTH: 72
<212> TYPE: DNA
<213> ORGANISM: Staphylococcus epidermidis

<400> SEQUENCE: 29
atgtacctgt aatcgctggt tctgcattaa aagcattaga aggcgatgct gaatacgaac    60
aaaaaatctt ag                                                        72

<210> SEQ ID NO 30
<211> LENGTH: 57
<212> TYPE: DNA
<213> ORGANISM: Staphylococcus epidermidis

<400> SEQUENCE: 30
atgtacctgt aatcgctggt tctgcattaa aagcattaga aggcgatgct gaatacg       57

<210> SEQ ID NO 31
<211> LENGTH: 51
<212> TYPE: DNA
<213> ORGANISM: Staphylococcus epidermidis

<400> SEQUENCE: 31
atgtacctgt aatcgctggt tctgcattaa aagcattaga aggcgatgct g             51

<210> SEQ ID NO 32
<211> LENGTH: 48
<212> TYPE: DNA
<213> ORGANISM: Staphylococcus epidermidis

<400> SEQUENCE: 32
atgtacctgt aatcgctggt tctgcattaa aagcattaga aggcgatg                 48

<210> SEQ ID NO 33
<211> LENGTH: 45
<212> TYPE: DNA
<213> ORGANISM: Staphylococcus epidermidis

<400> SEQUENCE: 33
atgtacctgt aatcgctggt tctgcattaa aagcattaga aggcg                    45

<210> SEQ ID NO 34
<211> LENGTH: 43
<212> TYPE: DNA
<213> ORGANISM: Staphylococcus epidermidis

<400> SEQUENCE: 34
atgtacctgt aatcgctggt tctgcattaa aagcattaga agg                      43

<210> SEQ ID NO 35
<211> LENGTH: 42
<212> TYPE: DNA
<213> ORGANISM: Staphylococcus epidermidis
```

<400> SEQUENCE: 35
atgtacctgt aatcgctggt tctgcattaa aagcattaga ag                42

<210> SEQ ID NO 36
<211> LENGTH: 39
<212> TYPE: DNA
<213> ORGANISM: Staphylococcus epidermidis
<220> FEATURE:
<223> OTHER INFORMATION: Staphylococcus epidermidis

<400> SEQUENCE: 36
atgtacctgt aatcgctggt tctgcattaa aagcattag                    39

<210> SEQ ID NO 37
<211> LENGTH: 33
<212> TYPE: DNA
<213> ORGANISM: Staphylococcus epidermidis

<400> SEQUENCE: 37
atgtacctgt aatcgctggt tctgcattaa aag                          33

<210> SEQ ID NO 38
<211> LENGTH: 24
<212> TYPE: DNA
<213> ORGANISM: Staphylococcus epidermidis

<400> SEQUENCE: 38
atgtacctgt aatcgctggt tctg                                    24

<210> SEQ ID NO 39
<211> LENGTH: 19
<212> TYPE: DNA
<213> ORGANISM: Staphylococcus epidermidis

<400> SEQUENCE: 39
atgtacctgt aatcgctgg                                          19

<210> SEQ ID NO 40
<211> LENGTH: 18
<212> TYPE: DNA
<213> ORGANISM: Staphylococcus epidermidis

<400> SEQUENCE: 40
atgtacctgt aatcgctg                                           18

<210> SEQ ID NO 41
<211> LENGTH: 15
<212> TYPE: DNA
<213> ORGANISM: Staphylococcus epidermidis

<400> SEQUENCE: 41
atgtacctgt aatcg                                              15

<210> SEQ ID NO 42
<211> LENGTH: 9
<212> TYPE: DNA
<213> ORGANISM: Staphylococcus epidermidis

<400> SEQUENCE: 42 atgtacctg                                                      9

<210> SEQ ID NO 43
<211> LENGTH: 20

```
<212> TYPE: DNA
<213> ORGANISM: Artificial
<220> FEATURE:
<223> OTHER INFORMATION: chemically synthesized

<400> SEQUENCE: 43
gtgaaattgt tgaaagggaa                                               20

<210> SEQ ID NO 44
<211> LENGTH: 18
<212> TYPE: DNA
<213> ORGANISM: Artificial
<220> FEATURE:
<223> OTHER INFORMATION: chemically synthesized

<400> SEQUENCE: 44
gactccttgg tccgtgtt                                                 18

<210> SEQ ID NO 45
<211> LENGTH: 19
<212> TYPE: DNA
<213> ORGANISM: Artificial
<220> FEATURE:
<223> OTHER INFORMATION: chemically synthesized

<400> SEQUENCE: 45
tccgtaggtg aacctgcgg                                                19

<210> SEQ ID NO 46
<211> LENGTH: 20
<212> TYPE: DNA
<213> ORGANISM: Artificial
<220> FEATURE:
<223> OTHER INFORMATION: chemically synthesized

<400> SEQUENCE: 46
gcatatcaat aagcggagga                                               20

<210> SEQ ID NO 47
<211> LENGTH: 57
<212> TYPE: DNA
<213> ORGANISM: Staphylococcus aureus

<400> SEQUENCE: 47
tattctcaat cactggtcgt ggtactgttg ctacaggccg tgttgaacgt ggtcaaa      57

<210> SEQ ID NO 48
<211> LENGTH: 57
<212> TYPE: DNA
<213> ORGANISM: Staphylococcus aureus

<400> SEQUENCE: 48
ataagagtta gtgaccagca ccatgacaac gatgtccggc acaacttgca ccagttt      57

<210> SEQ ID NO 49
<211> LENGTH: 120
<212> TYPE: DNA
<213> ORGANISM: Staphylococcus aureus

<400> SEQUENCE: 49
tcaaagttgg tgaagaagtt gaaatcatcg gtttacatga cacatctaaa acaactgtta  60
agtttcaacc acttcttcaa ctttagtagc caaatgtact gtgtagattt tgttgacaat  120

<210> SEQ ID NO 50
<211> LENGTH: 44
```

```
<212> TYPE: DNA
<213> ORGANISM: Staphylococcus aureus

<400> SEQUENCE: 50
caggtgttga aatgttccgt aaattattag actacgctga agct            44

<210> SEQ ID NO 51
<211> LENGTH: 44
<212> TYPE: DNA
<213> ORGANISM: Staphylococcus aureus

<400> SEQUENCE: 51
gtccacaact ttacaaggca tttaataatc tgatgcgact tcga            44

<210> SEQ ID NO 52
<211> LENGTH: 20
<212> TYPE: DNA
<213> ORGANISM: Artificial
<220> FEATURE:
<223> OTHER INFORMATION: chemically synthesized

<400> SEQUENCE: 52
tattctcaat cactggtcgt                                       20

<210> SEQ ID NO 53
<211> LENGTH: 17
<212> TYPE: DNA
<213> ORGANISM: Artificial
<220> FEATURE:
<223> OTHER INFORMATION: chemically synthesized

<400> SEQUENCE: 53
agcttcagcg tagtcta                                          17

<210> SEQ ID NO 54
<211> LENGTH: 25
<212> TYPE: DNA
<213> ORGANISM: Unknown
<220> FEATURE:
<223> OTHER INFORMATION: chemically synthesized

<400> SEQUENCE: 54
tcaaattttg agttgcatcc cctgg                                 25
```